US012797102B2

(12) United States Patent
Kwon et al.

(10) Patent No.: US 12,797,102 B2
(45) Date of Patent: Nov. 17, 2026

(54) HUMAN SOFT TISSUE CUTTING WIRE, AND METHOD FOR MANUFACTURING SAME

(71) Applicant: SMART WIRE CO., LTD., Goyang-si (KR)

(72) Inventors: Han Jin Kwon, Seoul (KR); Jung Ryul Ham, Paju-si (KR); Jae Min Kim, Seoul (KR); In Jong Kim, Seoul (KR)

(73) Assignee: SMART WIRE CO., LTD., Goyang-si (KR)

( * ) Notice: Subject to any disclaimer, the term of this patent is extended or adjusted under 35 U.S.C. 154(b) by 385 days.

(21) Appl. No.: 18/553,636

(22) PCT Filed: Apr. 21, 2022

(86) PCT No.: PCT/KR2022/005706
§ 371 (c)(1),
(2) Date: Oct. 2, 2023

(87) PCT Pub. No.: WO2022/225343
PCT Pub. Date: Oct. 27, 2022

(65) Prior Publication Data

US 2024/0180577 A1 Jun. 6, 2024

(30) Foreign Application Priority Data

Apr. 22, 2021 (KR) ........................ 10-2021-0052258

(51) Int. Cl.
*A61B 17/32* (2006.01)
*A61L 31/02* (2006.01)
(Continued)

(52) U.S. Cl.
CPC ............ *A61B 17/32* (2013.01); *A61L 31/022* (2013.01); *A61L 31/088* (2013.01); *B21F 7/00* (2013.01);
(Continued)

(58) Field of Classification Search
None
See application file for complete search history.

(56) References Cited

U.S. PATENT DOCUMENTS 4,981,756 A * 1/1991 Rhandhawa ........ C23C 14/0635 427/327
5,947,979 A * 9/1999 Ouchi .................... D07B 5/007 606/113
(Continued)

FOREIGN PATENT DOCUMENTS

CN 108103465 A * 6/2018 ........... C23C 14/352
JP H11104146 A * 4/1999
(Continued)

OTHER PUBLICATIONS

Machine Translation of JP-H11104146-A.*
(Continued)

*Primary Examiner* — David P Turocy
(74) *Attorney, Agent, or Firm* — Studebaker Brackett PLLC

(57) ABSTRACT

A wire for cutting human soft tissue and a manufacturing method thereof are disclosed. The method includes at least: forming a first stranded wire using a plurality of element wires; forming a second stranded wire using the first stranded wires; washing the second stranded wire with acetone and alcohol; mounting the second stranded wire, subjected to the third step, in a vacuum arc deposition system equipped with a cathodic arc source; forming a vacuum level of $10^{-6}$ Torr or less in the vacuum system;
(Continued)

cleaning the second stranded wire, subjected to the fourth step, in the vacuum system; and forming a hard coating layer of a compound containing titanium nitride (TiN) on the surface of the second stranded wire 3 at 400 °C in the vacuum system.

3 Claims, 8 Drawing Sheets

(51) Int. Cl.

| | |
|---|---|
| ***A61L 31/08*** | (2006.01) |
| ***B21F 7/00*** | (2006.01) |
| ***C23C 14/02*** | (2006.01) |
| ***C23C 14/06*** | (2006.01) |
| ***C23C 14/32*** | (2006.01) |
| ***C23C 14/58*** | (2006.01) |
| *A61B 17/00* | (2006.01) |

(52) U.S. Cl.

CPC ........ *C23C 14/021* (2013.01); *C23C 14/0641* (2013.01); *C23C 14/325* (2013.01); *C23C 14/58* (2013.01); *A61B 2017/00526* (2013.01); *A61B 2017/0088* (2013.01); *A61L 2420/02* (2013.01)

(56) References Cited

U.S. PATENT DOCUMENTS

| | | | | |
|---|---|---|---|---|
| 10,213,222 | B2 | 2/2019 | Guo et al. | |
| 2018/0334741 | A1 * | 11/2018 | Sukadhare | .......... C23C 14/0089 |
| 2020/0046400 | A1 | 2/2020 | Sato | |

FOREIGN PATENT DOCUMENTS

| | | | | | |
|---|---|---|---|---|---|
| KR | 10-2005-0069940 | A | | 7/2005 | |
| KR | 10-2013-0076420 | A | | 7/2013 | |
| KR | 20140006499 | A | * | 1/2014 | ............ C23C 14/24 |
| KR | 10-2014-0037450 | A | | 3/2014 | |
| KR | 10-2015-0007557 | A | | 1/2015 | |
| KR | 10-2017-0122037 | A | | 11/2017 | |

OTHER PUBLICATIONS

Huang, Da et al.; "Investigations in Anti-Impact Performance of TiN Coatings Prepared by Filtered Cathodic Vacuum Arc Method under Different Substrate Temperatures"; MDPI; Coatings; Aug. 28, 2020; vol. 10, No. 840; pp. 1-15.

International Search Report issued in PCT/KR2022/005706; mailed Aug. 8, 2022.

* cited by examiner

【 FIG. 1a】
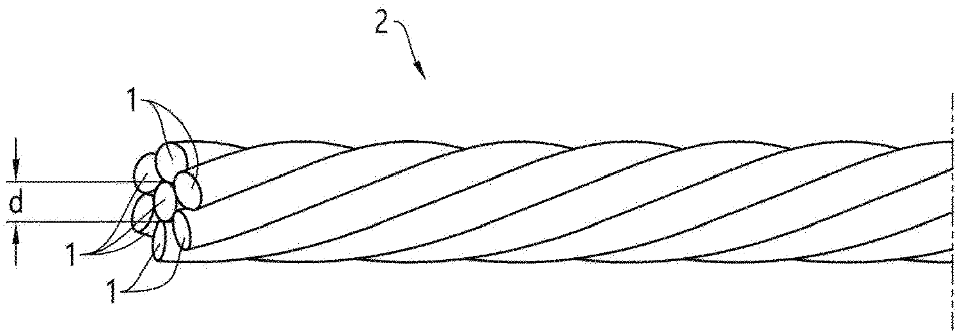

【 FIG. 1b】
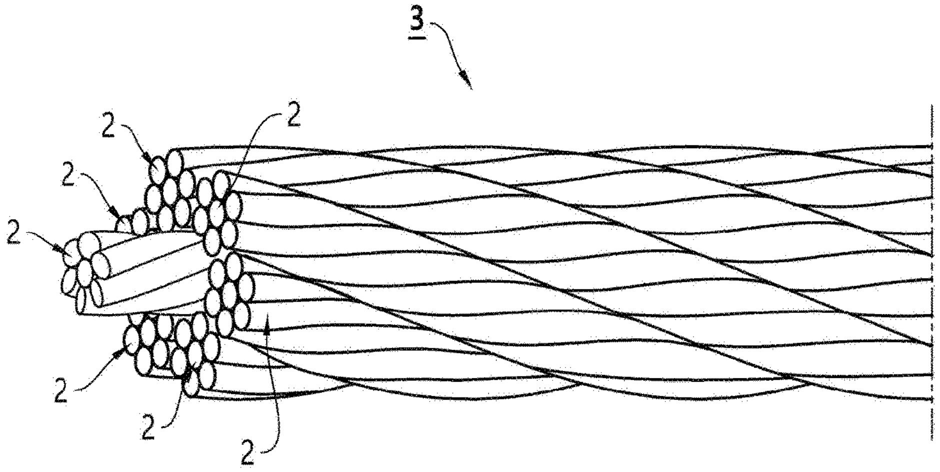

【FIG. 2】
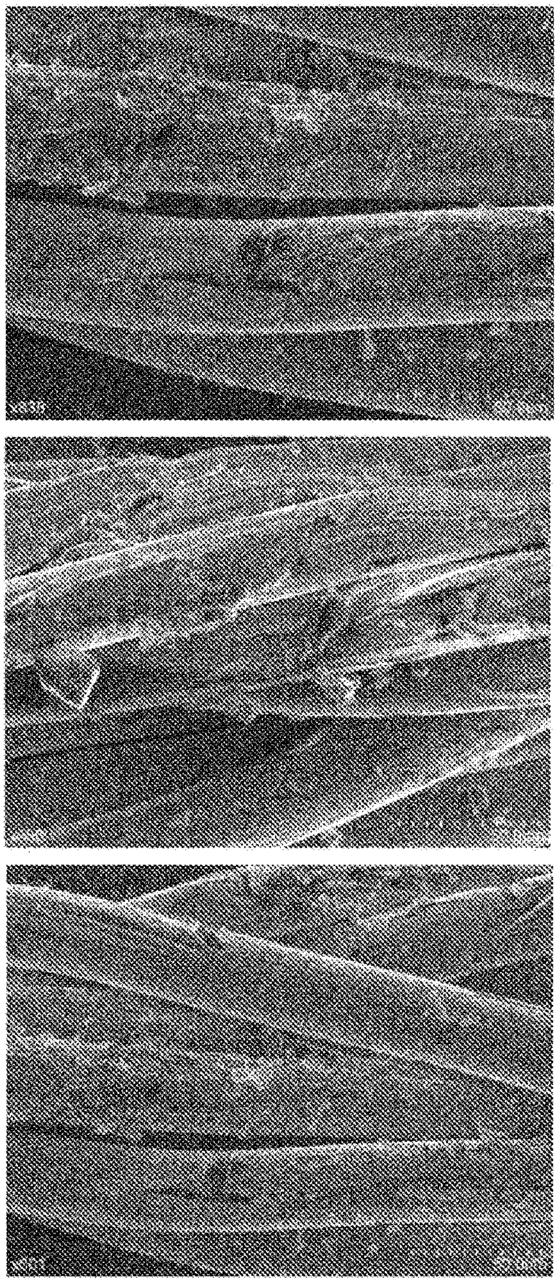

【FIG. 3】
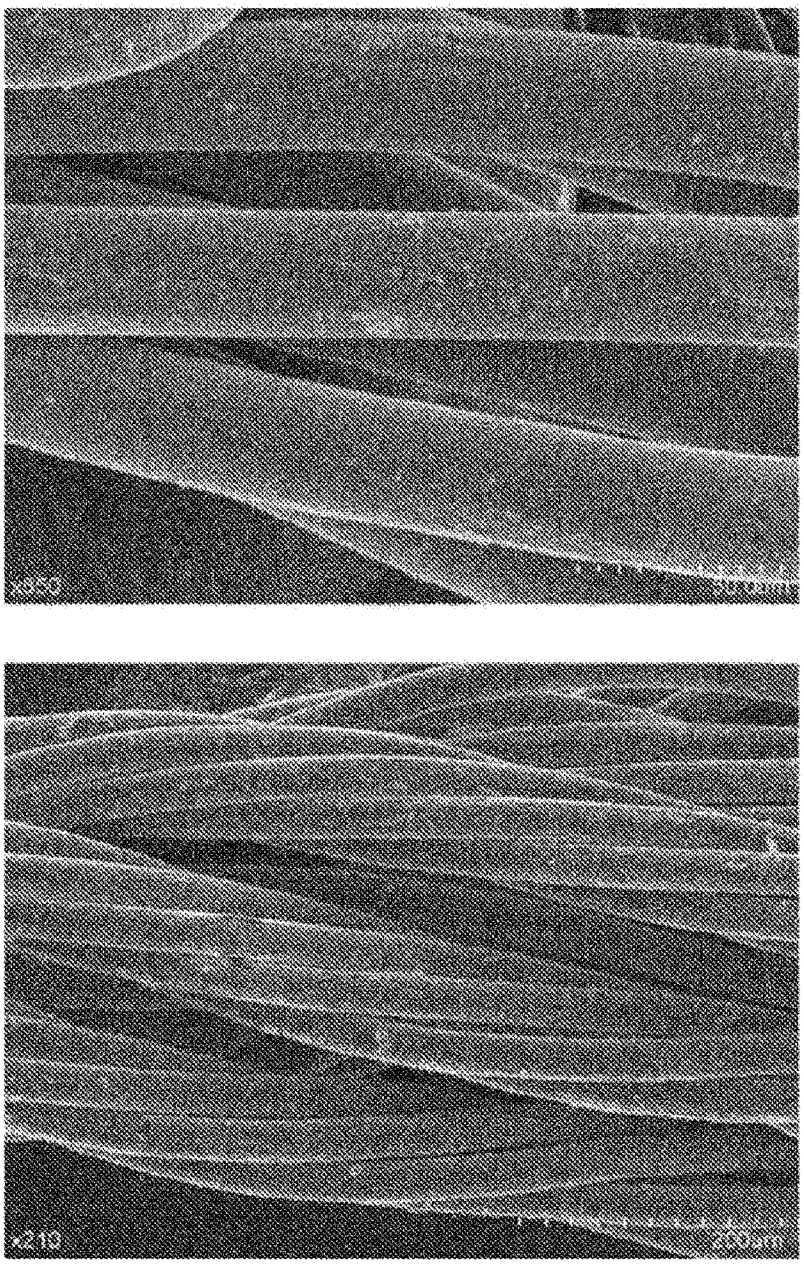

【FIG. 4】
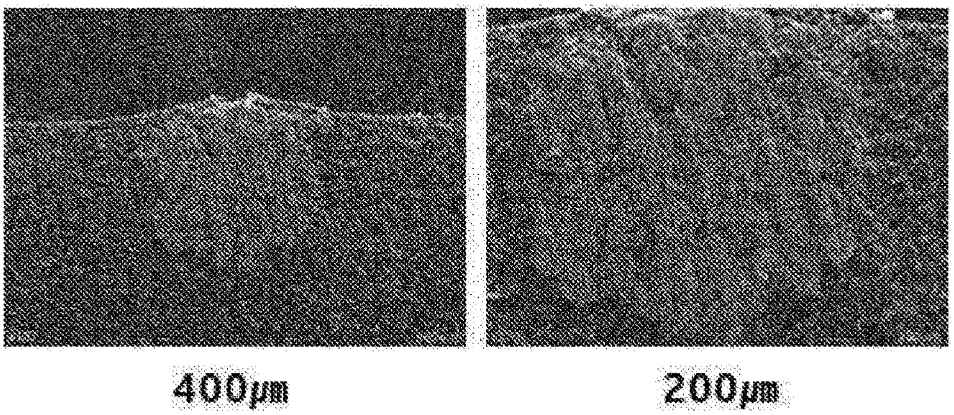

【FIG. 5】
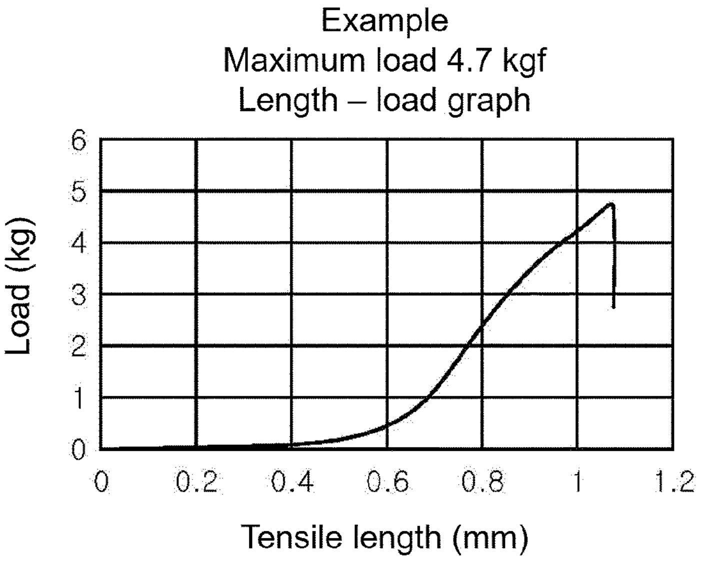
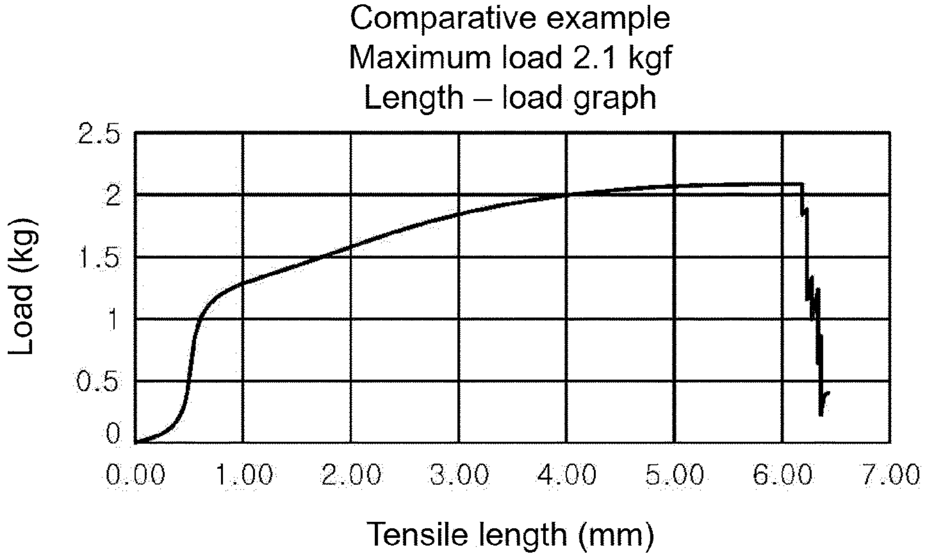

【FIG. 6a】
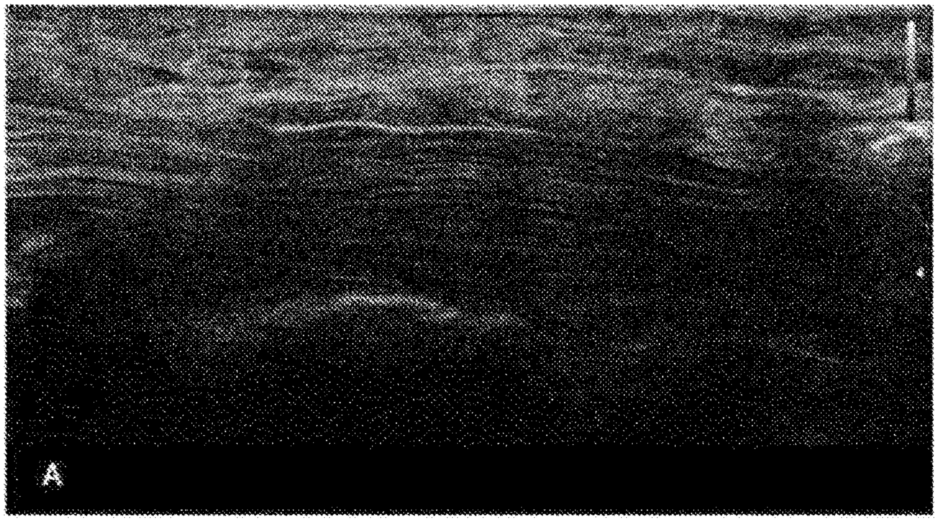

【FIG. 6b】
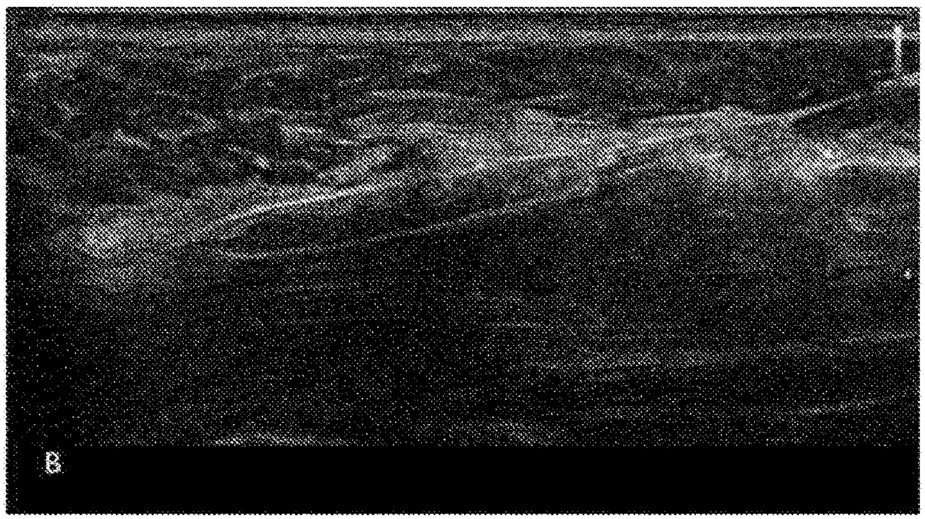

HUMAN SOFT TISSUE CUTTING WIRE, AND METHOD FOR MANUFACTURING SAME

CROSS-REFERENCE TO RELATED APPLICATIONS

This application is the U.S. National Stage of International Application No. PCT/KR2022/005706 filed Apr. 21, 2022, which claims benefit of priority to Korean Patent Application No. 10-2021-0052258 filed Apr. 22, 2021, the entire content of which is incorporated herein by reference.

TECHNICAL FIELD

The present invention relates to a cutting wire for cutting human soft tissue during a surgery or procedure and a manufacturing method thereof.

BACKGROUND ART

In general, during a surgery or procedure, the skin is incised, and organs are pushed aside to ensure a field of view and a space for operation so that the human tissue to be cut can be seen. In order to remove human soft tissue, a surgical procedure of cutting the soft tissue with a surgical knife is performed. However, this surgical procedure has disadvantages in that it can be burdensome to the doctor and requires a long recovery period for the patient.

As technology for overcoming the above disadvantages, U.S. Pat. No. 10,213,222 B2 is known. U.S. Pat. No. 10,213,222 B2 discloses a method for thread transection of soft tissue. The method for transection of soft tissue is a method in which a thread is pushed into the soft tissue to be cut through a minimum incision, and the tissue is cut by repeatedly moving the thread.

However, there are disadvantages in that, if the strength of the human tissue to be cut is high, the thread is broken, and if the thread is broken during a surgery or procedure, the surgery or procedure is difficult or inconvenient.

That is, although minimal invasive surgery still has advantages for both doctors and patients, there is a need to provide an improved thread configuration for soft tissue cutting so that minimal invasive surgery can be performed.

DISCLOSURE

Technical Problem

Therefore, an object of the present invention is to provide a wire for cutting human soft tissue, which may improve the convenience of surgery by having an increased cutting force, and a method for manufacturing the same.

Another object of the present invention is to provide a wire for cutting human soft tissue, which is non-toxic and harmless to the human body and does not leave foreign substances in the human body during a process of cutting human soft tissue, and a method for manufacturing the same.

Technical Solution

A wire for cutting human soft tissue and a manufacturing method thereof according to an embodiment of the present invention to achieve the above objects include: a first step (S1) of forming a first stranded wire 2 using a plurality of element wires 1; a second step (S2) of forming a second stranded wire 3 using the first stranded wires 2; a third step (S3) of washing the second stranded wire 3 with acetone and alcohol; a fourth step (S4) of mounting the second stranded wire 3, subjected to the third step (S3), in a vacuum arc deposition system equipped with a cathodic arc source; a fifth step (S5) of creating a vacuum of $10^{-6}$ Torr or less in the vacuum system; a sixth step (S6) of cleaning the second stranded wire 3, subjected to the fourth step (S4), in the vacuum system; and a seventh step (S7) of forming a hard coating layer of a compound containing titanium nitride (TiN) on the surface of the second stranded wire 3 at 400 °C in the vacuum system.

In the wire for cutting human soft tissue and manufacturing method thereof according to the embodiment of the present invention, the first stranded wire 2 may be formed by disposing one element wire 1 at the center, disposing six element wires 1 around the element wire 1 disposed at the center, and twisting a total of seven element wires 1, and the second stranded wire 3 may be formed by disposing one first stranded wire 2 at the center, disposing six first stranded wires 2 around the first stranded wire 2 disposed at the center, and twisting a total of seven first stranded wires 2.

In the wire for cutting human soft tissue and manufacturing method thereof according to the embodiment of the present invention, the element wire 1 may have a thickness of 26 to 28 μm and may be made of stainless steel.

In the wire for cutting human soft tissue and manufacturing method thereof according to the embodiment of the present invention, the second stranded wire 3 may have a thickness of 262 to 280 μm.

In the wire for cutting human soft tissue and manufacturing method thereof according to the embodiment of the present invention, the second stranded wire 3 may have a thickness of 268 to 272 μm.

Specific details of other embodiments are included in the following detailed description and the accompanying drawings.

Advantageous Effects

The above-described wire for cutting human soft tissue manufactured by the method for manufacturing a wire for human soft tissue according to the embodiment of the present invention is manufactured by forming the first stranded wire using a plurality of element wires, forming the second stranded wire using a plurality of the first stranded wires, and coating the second stranded wire with titanium nitride (TiN). Thus, the wire for cutting human soft tissue has significantly increased rigidity, excellent wear resistance, excellent cutting performance, and excellent ultrasound visibility, compared to conventional threads for cutting human soft tissue.

In addition, since the wire for cutting human soft tissue manufactured by the method for manufacturing a wire for human soft tissue according to the embodiment of the present invention is manufactured by coating a bundle of element wires with titanium nitride (TiN), it is harmless to the human body and does not leave foreign substances in the human body when used to cut human soft tissue.

BRIEF DESCRIPTION OF DRAWINGS

FIG. 1 illustrates the configuration of a wire for cutting human soft tissue according to an embodiment of the present invention.

FIG. 2 shows photographs taken with an electron microscope after a wear resistance test for a wire for cutting human soft tissue according to an embodiment of the present invention, which is not coated with titanium nitride.

FIG. 3 shows photographs taken with an electron microscope after a wear resistance test for a wire for cutting human soft tissue according to an embodiment of the present invention, which is coated with titanium nitride.

FIG. 4 depicts electron micrographs showing the cross-section of a wire for cutting human soft tissue according to an embodiment of the present invention after coating with titanium nitride.

FIG. 5 is a graph showing the results of measuring the maximum load using a tensile tester to evaluate the effect of a wire for cutting human soft tissue according to an embodiment of the present invention.

FIG. 6 shows ultrasound images of a wire for cutting human soft tissue according to an embodiment of the present invention before and after coating with titanium nitride.

MODE FOR INVENTION

The advantages and features of the present invention, and the way of attaining them, will become apparent with reference to the exemplary embodiments described below in conjunction with the accompanying drawings.

Hereinafter, embodiments of the present invention will be described in detail with reference to the accompanying drawings. The embodiments described below are presented by way of example to assist in the understanding of the present invention, and it should be understood that the present invention may be embodied in various modified forms different from the embodiments described herein. In the following description, the detailed description of related known functions and configurations will be omitted when it may unnecessarily obscure the subject matter of the present invention. In addition, the accompanying drawings are not necessarily to scale and in some instances, proportions may have been exaggerated in order to help understand the present invention.

Meanwhile, terms such as first, second, etc. may be used to describe various components, but the components should not be limited by the terms. These terms are used only to distinguish one component from another component. For example, a first component may be termed a second component without departing from the scope of the present invention, and similarly, a second component may also be termed a first component.

Meanwhile, the terms to be described later are terms selected in consideration of their functions in the present invention, but they may change depending on the intents of those skilled in the art, or precedents. Accordingly, these terms should be defined based on the entire contents of the present specification.

Throughout the specification, like reference numerals designate like components.

Hereinafter, a wire for cutting human soft tissue and a method for manufacturing the same according to an embodiment of the present invention will be described with reference to FIGS. 1 to 6. FIG. 1 illustrates the configuration of a wire for cutting human soft tissue according to an embodiment of the present invention. FIG. 2 shows photographs taken with an electron microscope after a wear resistance test for a wire for cutting human soft tissue according to an embodiment of the present invention, which is not coated with titanium nitride. FIG. 3 shows photographs taken with an electron microscope after a wear resistance test for a wire for cutting human soft tissue according to an embodiment of the present invention, which is coated with titanium nitride. FIG. 4 depicts electron micrographs showing the cross-section of a wire for cutting human soft tissue according to an embodiment of the present invention after coating with titanium nitride. FIG. 5 is a graph showing the results of measuring the maximum load using a tensile tester to evaluate the effect of a wire for cutting human soft tissue according to an embodiment of the present invention. FIG. 6 shows ultrasound images of a wire for cutting human soft tissue according to an embodiment of the present invention before and after coating with titanium nitride.

A wire for cutting human soft tissue and a manufacturing method thereof according to an embodiment of the present invention will be described step by step.

In a first step (S1), as shown in FIG. 1*a*, a plurality of element wires are twisted to form a first stranded wire 2.

In the second step S2, as shown in FIG. 1*b*, the first twisted wires 2 are twisted to form a second stranded wire 3.

In the wire for cutting human soft tissue according to an embodiment of the present invention, the rigidity of the cutting wire may be greatly increased through the first and second steps (S1 and S2).

A third step (S3) is a step of cleaning the second stranded wire 3 with acetone and alcohol. By performing the cleaning step, foreign substances may be removed more reliably, and there may be no residue on the surface of the cutting wire after completion of the cleaning.

A fourth step (S4) is a step of mounting the second stranded wire 3, subjected to the third step (S3), in a vacuum arc deposition system equipped with a cathodic arc source. Since the arc deposition system is known technology, detailed description thereof will be omitted.

A fifth step (S5) is a step of creating a vacuum of $10^{-6}$ Torr or less in the vacuum system. As the level of the vacuum becomes lower, it is possible to more reliably prevent ultra-fine dust or ultra-fine foreign matter from adhering to the second stranded wire 3.

A sixth step (S6) is a step of cleaning the second stranded wire 3 subjected to the fourth step S4 in the vacuum system.

A seventh step (S7) is a step of forming a hard coating layer of a compound containing titanium nitride (TiN) on the surface of the second stranded wire 3 at 400 °C in the vacuum system.

When the surface of the second stranded wire 3 is coated with titanium nitride, the cutting force may be increased and the wear resistance may be significantly increased.

FIG. 2 shows a state in which the surface of the second stranded wire 3 is not coated with titanium nitride, and FIG. 3 shows a state in which the surface of the second stranded wire 3 is coated with titanium nitride.

In FIG. 2, it can be seen that there are protrusions or deformed shapes on the surface of the second stranded wire 3, but in FIG. 3, it can be seen that the surface of the second stranded wire 3 is relatively smooth.

In addition, as a result of performing a tensile test, as shown in FIG. 5, it can be seen that an example coated with titanium nitride had a very high maximum load of 4.7 kgf, but a comparative example not coated with titanium nitride had a relatively low maximum load of 2.1 kgf.

That is, the wire for cutting human soft tissue manufactured by the method for manufacturing a wire for cutting human soft tissue according to an embodiment of the present invention has very strong rigidity and is extremely unlikely to be broken during a surgery or procedure.

In addition, when a procedure or surgery is performed using the wire for cutting human soft tissue manufactured by the method for manufacturing a wire for cutting human soft tissue according to an embodiment of the present invention, the cutting wire is clearly displayed on the ultrasound image as can be seen in FIG. 6.

When a procedure or surgery is performed using the second stranded wire 3 (cutting wire) not coated with titanium nitride, it is difficult to identify the cutting wire, as shown in FIG. 6*a*.

On the other, when a procedure or surgery is performed using the second stranded wire 3 (cutting wire) coated with titanium nitride, it is possible to clearly identify the cutting wire, as shown in FIG. 6*b*.

Meanwhile, as shown in FIG. 1*a*, the first stranded wire 2 may be formed by disposing one element wire 1 at the center, disposing six element wires 1 for winding around the element wire 1 disposed at the center, and twisting a total of seven element wires 1.

In addition, as shown in FIG. 1*b*, the second stranded wire 3 may be formed by disposing one first stranded wire 2 at the center, disposing six first stranded wires 2 for winding around the first stranded wire 2 disposed at the center, and twisting a total of seven first stranded wires 2.

That is, the wire for cutting human soft tissue according to an embodiment of the present invention is manufactured by forming the first stranded wire 2 using seven element wires and forming the second stranded wire 3 using seven first stranded wires 2. Accordingly, the second stranded wire 3 may consist of 49 element wires 1, and thus the rigidity of the second stranded wire 3 may be increased, and it is possible to avoid the problem that the cutting wire is broken during a surgery or procedure.

Meanwhile, the element wire 1 may have a thickness of 26 to 28 μm and be made of stainless steel. In this case, the wire for cutting human soft tissue according to an embodiment of the present invention may maintain good quality without being corroded.

Meanwhile, the second stranded wire 3 may consist of 49 element wires, and when viewed in the cross-section of the second stranded wire 3, seven element wires may be disposed at the center and fine voids may be formed. That is, the second stranded wire 3 may have a thickness of 262 to 280 μm.

When the thickness of the second stranded wire 3 is 262 μm or more, voids between the element wires 1 may accommodate the deformed displacement while the element wires 1 are twisted during manufacturing of the first and second stranded wires 2 and 3.

In addition, when the second stranded wire 3 has a thickness of 280 μm or less, it may exhibit good cutting performance.

Meanwhile, the thickness of the second stranded wire 3 may be 268 to 272 μm. In this case, the second stranded wire 3 may have further improved cutting performance due to its small thickness, and when the first and second stranded wires 2 and 3 are manufactured by twisting the element wires 1, even though the element wires 1 are in close contact, each element wire 1 is not broken and the first and second stranded wires 2 and 3 may be manufactured satisfactorily.

Therefore, the wire for cutting human soft tissue according to an embodiment of the present invention has a very small thickness of 262 to 280 μm, more specifically 268 to 272 μm, even though the second stranded wire 3 is manufactured by twisting 49 element wires. Accordingly, the wire for cutting human soft tissue may exhibit a good ability to cut human soft tissue and may maintain very high rigidity.

Meanwhile, in the method for manufacturing a wire for cutting human soft tissue according to an embodiment of the present invention, the seventh step (S7) may include subjecting the second stranded wire 3 (cutting wire) to an etching process in an argon (Ar) plasma environment.

The titanium nitride (TiN) is non-toxic and is suitable for application to the body, and is extremely hard so that it may greatly increase the strength of the cutting wire surface is greatly increased to eliminate a phenomenon in which foreign matter remains in the body due to wear during the cutting process, and greatly increase the cutting force.

In addition, the wire for cutting human soft tissue according to an embodiment of the present invention may have improved ultrasound visibility.

In particular, the wire for cutting human soft tissue according to an embodiment of the present invention may greatly increase the convenience of surgery by easily cutting the soft tissue inside the body after being inserted under the skin.

Hereinafter, a process of manufacturing the wire for cutting human soft tissue according to an embodiment of the present invention will be described in more detail with reference to tables.

For the element wire 1, a steel grade (STS 316L) is applied considering the strand processing and coating processes, and the element wire 1 used has a very small thickness of 26 to 28 μm. Comparative data for steel grades are shown in Tables 1 and 2 below.

TABLE 1

| Comparison of chemical components between steel grades 316L and 316LVAR (unit: wt %) | | | | | | | | | | | |
|---|---|---|---|---|---|---|---|---|---|---|---|
| Steel grade | | C | Si | Mn | P | S | Ni | Cr | Mo | N | Cu |
| 316L | Min | — | — | — | — | — | 12.00 | 16.00 | 2.00 | — | — |
| | Max | 0.030 | 1.00 | 2.00 | 0.045 | 0.030 | 15.00 | 18.00 | 3.00 | — | — |
| 316LVAR | Min | — | — | — | — | — | 13.00 | 17.00 | 2.25 | — | — |
| | Max | 0.030 | 0.75 | 2.00 | 0.250 | 0.010 | 15.00 | 19.00 | 3.00 | 0.10 | 0.50 |

* 316L: according to JIS G 4308; 316LVAR: according to ASTM F138

TABLE 2

| Comparison of mechanical properties between steel grades 316L and 316LVAR | | | |
|---|---|---|---|
| | CWHF | PRE | P value |
| 316L | 93.96 | 23 | 192 |
| 316LVAR | 81 | 27 | 91 |

CWHF (Cold Work Hardening Factor) is an index in which strength is increased due to work hardening and transformation-induced martensitic structure formation during cold working. A steel grade with a higher CWTF index has higher work hardenability. The work hardenability of 316L is greater than that of 316LVAR.

PRE (Pitting Resistance Equivalent) represents the pitting resistance index, and the larger the index value, the stronger the corrosion resistance. In other words, 316LVAR has stronger corrosion resistance than 316L.

The P Value is an index representing magnetism, and the lower the P value, the lower the magnetism. The magnetic strength of 316L is greater than that of 316LVAR.

The first stranded wire 2 is made by uniformly twisting seven element wires 1 of stainless steel (STS) 316L. The seven first stranded wires 2 are uniformly twisted again to make the second stranded wire 3. The second stranded wire 3 is hereinafter referred to as the ' cutting wire' and will be described in detail with reference to Table 3 below and FIG. 1.

TABLE 3

| Specification of second stranded wire (cutting wire) | | | |
|---|---|---|---|
| Description | Stainless steel wire rope | Structure | 7 × 7 |
| Grade | STS 316L | Diameter | 262 to 280 μm |

In addition, a compound containing titanium nitride (TiN) is used as a raw material for the coating layer. Detailed information on the component analysis results and configuration of the wire rope after formation of the hard coating layer is shown in Tables 4 and 5 below.

TABLE 4

| Component analysis of cutting wire (unit: wt %) | | | | | | | | |
|---|---|---|---|---|---|---|---|---|
| | Chemical components | | | | | | | |
| | C | Si | Mn | P | S | Ni | Cr | Mo |
| (%) | 0.0150 | 0.2500 | 0.8400 | 0.0300 | 0.0010 | 12.0900 | 16.7200 | 2.0100 |

TABLE 5

| Standards and test results for cutting wire | | |
|---|---|---|
| Test items | Standards | Test results |
| Wire diameter | 260 to 290 μm | 271 μm |
| Tensile strength | At least 5.00 kgf | 5.4 kgf |
| Twist length | 2.00 mm | 1.98 mm |
| Twist length of outer strand | 1.08 mm | 1.01 mm |
| Preform | — | Good |

First, the cutting wire is ultrasonically cleaned with alcohol and acetone. The cleaned cutting wire is mounted in a vacuum arc deposition system, and the inside of the vacuum system is evacuated to create a vacuum. At this time, the level of the vacuum is $10^{-6}$ Torr or less.

Next, the cutting wire mounted in the vacuum system is cleaned and a hard coating layer is formed on the cutting wire. To form the coating layer, argon (Ar) gas may be injected into the vacuum system to increase the vacuum level.

When the vacuum level after gas injection reaches $7\times10^{-4}$ Torr, the cathodic arc source equipped with the titanium target is power-activated and voltage is applied to the cutting wire to proceed with cleaning.

After the cleaning process for the cutting wire is completed, argon (Ar) gas and nitrogen (N) gas are injected into the system and the same pressure as in wire rope cleaning is applied to form a compound coating layer containing titanium nitride (TiN).

After coating to the desired thickness or shape is completed, a voltage of about 100 V is applied to the cutting wire to the uppermost coating layer, and the coating process is completed.

Although embodiments of the present invention have been described above, the scope of the present invention is not limited to the above embodiments.

The results of comparing Examples and Comparative Examples conducted for the present invention under different conditions are shown in Table 6 below.

Table 6 below shows the differences between Examples 1 to 3 and Comparative Examples 1 to 3, including the coating process temperature, the presence or absence and type of etching, the coating thickness, etc., which result in differences in the maximum load, elasticity, cutting force, etc. between cutting wires.

TABLE 6

| Items | | Example 1 | Example 2 | Example 3 | Comparative Example 1 | Comparative Example 2 | Comparative Example 3 |
|---|---|---|---|---|---|---|---|
| Coating | | TiN coating #1 | TiN coating #2 | TiN coating #3 | TiN coating #4 | TiN coating #5 | X |
| Coating conditions | | Etching X | Etching Ar plasma | Etching Filament | Etching X | Etching Arc plasma | X |
| | | Temp. 400 °C | Temp. 400 °C | Temp. 400 °C | Temp. 600 °C | Temp. 600 °C | |
| Coating thickness | | About 1 μm | About 1 μm | About 1 μm | About 1 μm | 3 to 5 μm | X |
| Strength at break | | 47 N | 35 to 45 N | 35 to 45 N | 35 to 45 N | 20 to 25 N | 42.4 N |
| Maximum load | | 4.5 to 5.0 kgf | 3.5 to 4.5 kgf | 3.5 to 4.5 kgf | 3.5 to 4.5 kgf | 2.0 to 2.5 kgf | 4.5 to 5.0 kgf |
| Elasticity | | Maintained | Maintained | Maintained | Maintained | Lost | Maintained |
| Procedure results | Cutting force | 5 | 4.5 | 4 | 3 | 1 | 2 |
| | Ultrasound visibility | 5 | 4.5 | 4.5 | 4 | 4 | 2 |

* Explanation of procedure result numbers: 5: very good, 4: good, 3: moderate, 2: poor, and 1: very poor
* Etching: etching process refers to a process that removes unnecessary parts while leaving only necessary parts on the surface.
* Tensile strength calculation formula: Tensile strength = maximum load/cross-sectional area of specimen Example 1 was not etched and was coated with a compound containing titanium nitride (TiN) at 400 °C. It is evaluated that Example 1 did not slip during a procedure, had excellent cutting force, and had a higher maximum load than the other Examples and Comparative Examples. In addition, Example 1 showed a clear and excellent cutting wire image quality on the ultrasound image compared to before coating. Additionally, Example 1 maintained good elasticity.

Example 2 was etched using argon (Ar) plasma at 400 °C and coated with a compound containing titanium nitride (TiN). Example 2 is evaluated to have a lower cutting force and maximum load than Example 1. In addition, Example 2 showed a clear and excellent cutting wire image quality on the ultrasound image compared to before coating. Additionally, Example 2 maintained good elasticity.

Example 3 was etched using a filament at 400 °C and coated with a compound containing titanium nitride (TiN). Example 3 is evaluated to have a lower cutting force and a similar maximum load compared to Examples 1 and 2. In addition, Example 3 showed a clear and excellent cutting wire image quality on the ultrasound image compared to before coating. Additionally, Example 3 maintained good elasticity.

Comparative Example 1 was not etched and was coated with a compound containing titanium nitride (TiN) at 600 °C. Comparative Example 1 is evaluated to have a lower cutting force and a similar maximum load compared to Example 3. In addition, Comparative Example 1 showed a clear and excellent cutting wire image quality on the ultrasound image compared to before coating. Additionally, Comparative Example 1 maintained good elasticity.

Comparative Example 2 was etched using arc plasma at 600 °C and coated with a compound containing titanium nitride (TiN). Comparative Example 2 is evaluated to have a very lower cutting force and maximum load than Comparative Example 1. In addition, Example 2 showed a clear and excellent cutting wire image quality on the ultrasound image compared to before coating. Additionally, Example 2 maintained good elasticity. In particular, Comparative Example 2 was easily broken compared to the specimen before coating. In addition, Comparative Example 2 showed a clear and good cutting wire image quality on the ultrasound image compared to before coating. In addition, Comparative Example 2 lost elasticity.

Comparative Example 3 was not coated with a compound containing titanium nitride (TiN) and was not etched. Comparative Example 3 is evaluated to have an excellent maximum load but have an excessively low cutting force during procedure. In addition, Comparative Example 3 showed a faint and poor cutting image quality on the ultrasound image. Additionally, Comparative Example 3 maintained elasticity.

While the embodiments of the present invention have been described with reference to the accompanying drawings, it will be understood by those skilled in the art to which the present invention pertains that the present invention may be embodied in other specific forms without departing from the technical spirit or essential characteristics of the present invention.

Therefore, the embodiments described above are considered to be illustrative in all respects and not restrictive. Furthermore, the scope of the present invention is defined by the appended claims, and it should be understood that all modifications or variations derived from the meanings and scope of the claims and equivalents thereto are included within the scope of the present invention.

Embodiments of the present invention may provide a method for manufacturing a cutting wire for cutting human soft tissue and a cutting wire manufactured thereby.

The invention claimed is:

1. A method of using a wire for cutting human soft tissue, the method comprising:

a first step of forming a first stranded wire using a plurality of element wires;

a second step of forming a second stranded wire using the first stranded wires;

a third step of washing the second stranded wire with acetone and alcohol;

a fourth step of mounting the second stranded wire, subjected to the third step, in a vacuum arc deposition system equipped with a cathodic arc source;

a fifth step of creating a vacuum of 10-6 Torr or less in the vacuum arc deposition system;

a sixth step of cleaning the second stranded wire, subjected to the fourth step, in the vacuum arc deposition system;

a seventh step of forming a hard coating layer of a compound containing titanium nitride (TiN) on a surface of the second stranded wire at 400 °C in the vacuum arc deposition system to obtain the wire for cutting human soft tissue; and an eighth step of using the wire, wherein the wire is pushed into human soft tissue and repeatedly moved to cut human soft tissue, wherein the element wire has a thickness of 26 to 28 μm and is made of stainless steel, wherein the first stranded wire is formed by disposing one element wire at a center, disposing six element wires around the element wire disposed at the center, and twisting a total of seven element wires, wherein the second stranded wire is formed by disposing one first stranded wire at a center, disposing six first stranded wires around the first stranded wire disposed at the center, and twisting a total of seven first stranded wires, wherein the second stranded wire has a thickness of 268 to 272 μm, and wherein the hard coating layer of titanium nitride (TiN) provides improved ultrasound visibility of the second stranded wire during a surgical procedure.

2. The method of claim 1, wherein the element wires are twisted in close contact without breakage of the element wires.

3. The method of claim 1, wherein the vacuum of $10^{-6}$ Torr or less is created to prevent adhesion of ultra-fine dust and foreign matter to the second stranded wire.

* * * * *